(12) United States Patent
Kwok et al.

(10) Patent No.: US 9,005,985 B2
(45) Date of Patent: *Apr. 14, 2015

(54) OPTICAL REPORTER COMPOSITIONS

(71) Applicant: APDN (B.V.I.) Inc., Tortola (VG)

(72) Inventors: Thomas Kwok, Miller Place, NY (US); Benjamin MingHwa Liang, East Setauket, NY (US); Stephane Shu Kin So, South Portland, ME (US)

(73) Assignee: APDN (B.V.I.) Inc., Stony Brook, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/761,447

(22) Filed: Feb. 7, 2013

(65) Prior Publication Data

US 2013/0149706 A1 Jun. 13, 2013

Related U.S. Application Data

(63) Continuation of application No. 11/954,030, filed on Dec. 11, 2007, now Pat. No. 8,372,648, which is a continuation-in-part of application No. 11/437,265, filed on May 19, 2006, now abandoned, said (Continued)

(51) Int. Cl.
*C12Q 1/68* (2006.01)
*C09D 7/12* (2006.01)
(Continued)

(52) U.S. Cl.
CPC .............. *C12Q 1/6876* (2013.01); *C08K 5/09* (2013.01); *C09D 7/1233* (2013.01); *C09D 11/03* (2013.01); *C12Q 1/6816* (2013.01); *B82Y 15/00* (2013.01); *Y10S 977/774* (2013.01); *Y10S 977/92* (2013.01)

(58) Field of Classification Search
CPC .......... C08K 5/09; C09D 7/233; C09D 11/03; C12Q 1/6816; Y10S 977/92; Y10S 977/977; Y10S 977/774
USPC ............. 435/6.11, 6.12; 977/774, 920; 33/53, 33/543
See application file for complete search history.

(56) References Cited

U.S. PATENT DOCUMENTS 4,183,989 A 1/1980 Tooth
4,739,044 A 4/1988 Stabinsky
(Continued)

FOREIGN PATENT DOCUMENTS

CN WO 98/06084 A1 2/1998
EP WO 03/030129 4/2003
(Continued)

OTHER PUBLICATIONS

Louis V. Wollenberger, et al., "Detection of DNA using upconverting phosphor reporter phobes", SPIE vol. 2985, pp. 100-111.
(Continued)

*Primary Examiner* — Rebecca M Fritchman
(74) *Attorney, Agent, or Firm* — Algis Anilionis; Sean R. Wilsusen; F. Chau & Associates, LLC

(57) ABSTRACT

This invention provides compositions that have a light emitting reporter linked to biomolecules, preferably, nucleotide oligomers. The light reporter particles are silylated and functionalized to produce a coated light reporter particle, prior to covalently linking the biomolecules to the light reporter particle. The light reporter particles of the invention can be excited by a light excitation source such as UV or IR light, and when the biomolecule is DNA, the attached DNA molecule(s) are detectable by amplification techniques such as PCR.

21 Claims, 2 Drawing Sheets

Related U.S. Application Data application No. 11/954,030 is a continuation-in-part of application No. 10/825,968, filed on Apr. 15, 2004, now abandoned, and a continuation-in-part of application No. 11/954,038, filed on Dec. 11, 2007, now Pat. No. 8,426,216, and a continuation-in-part of application No. 11/954,009, filed on Dec. 11, 2007, now Pat. No. 8,124,333, and a continuation-in-part of application No. 11/954,044, filed on Dec. 11, 2007, now Pat. No. 8,415,164, and a continuation-in-part of application No. 11/954,051, filed on Dec. 11, 2007, now Pat. No. 8,415,165, and a continuation-in-part of application No. 11/954,055, filed on Dec. 11, 2007, now Pat. No. 8,420,400.

(60) Provisional application No. 60/682,976, filed on May 20, 2005, provisional application No. 60/463,215, filed on Apr. 16, 2003, provisional application No. 60/874,425, filed on Dec. 12, 2006, provisional application No. 60/877,869, filed on Dec. 29, 2006, provisional application No. 60/877,875, filed on Dec. 29, 2006.

(51) Int. Cl.
  *C09D 11/03* (2014.01)
  *C12Q 1/00* (2006.01)
  *C08K 5/09* (2006.01)
  *B82Y 15/00* (2011.01)

(56) References Cited

U.S. PATENT DOCUMENTS

| | | |
|---|---|---|
| 4,757,141 A | 7/1988 | Fung et al. |
| 5,047,519 A | 9/1991 | Hobbs, Jr. et al. |
| 5,132,242 A | 7/1992 | Cheung |
| 5,139,812 A | 8/1992 | Lebacq |
| 5,151,507 A | 9/1992 | Hobbs, Jr. et al. |
| 5,429,952 A | 7/1995 | Garner et al. |
| 5,602,381 A | 2/1997 | Hoshino et al. |
| 5,639,603 A | 6/1997 | Dower et al. |
| 5,763,176 A | 6/1998 | Slater et al. |
| 5,776,713 A | 7/1998 | Garner et al. |
| 5,866,336 A | 2/1999 | Nazarenko et al. |
| 5,942,444 A | 8/1999 | Rittenburg et al. |
| 5,989,823 A | 11/1999 | Jayasena et al. |
| 6,030,657 A | 2/2000 | Butland et al. |
| 6,057,370 A | 5/2000 | Weiland et al. |
| 6,127,120 A | 10/2000 | Graham et al. |
| 6,140,075 A | 10/2000 | Russell et al. |
| 6,169,174 B1 | 1/2001 | Hasewaga et al. |
| 6,312,911 B1 | 11/2001 | Bancroft et al. |
| 6,326,489 B1 | 12/2001 | Church et al. ............... 536/25.3 |
| 6,342,359 B1 | 1/2002 | Lee et al. |
| 6,361,944 B1 | 3/2002 | Mirkin et al. |
| 6,399,397 B1 | 6/2002 | Zarling et al. |
| 6,576,422 B1 | 6/2003 | Weinstein et al. |
| 6,686,149 B1 | 2/2004 | Sanchis et al. |
| 6,743,640 B2 | 6/2004 | Whitten et al. |
| 6,995,256 B1 | 2/2006 | Li et al. |
| 7,060,874 B2 | 6/2006 | Wilkins |
| 7,115,301 B2 | 10/2006 | Sheu et al. |
| 7,160,996 B1 | 1/2007 | Cook |
| 7,223,906 B2 | 5/2007 | Davis |
| 2002/0048822 A1 | 4/2002 | Rittenburg et al. |
| 2002/0056147 A1 | 5/2002 | Dau et al. |
| 2002/0187263 A1 | 12/2002 | Sheu et al. |
| 2003/0142704 A1 | 7/2003 | Lawandy |
| 2003/0142713 A1 | 7/2003 | Lawandy |
| 2003/0162296 A1 | 8/2003 | Lawandy |
| 2003/0177095 A1 | 9/2003 | Zorab et al. |
| 2003/0207331 A1* | 11/2003 | Wilson et al. ............... 435/7.1 |
| 2004/0063117 A1 | 4/2004 | Rancien et al. |
| 2004/0166520 A1 | 8/2004 | Connolly |
| 2004/0219287 A1 | 11/2004 | Regan et al. |
| 2005/0059059 A1 | 3/2005 | Liang |
| 2005/0136486 A1 | 6/2005 | Haushalter ............... 435/7.2 |
| 2005/0214532 A1 | 9/2005 | Kosak et al. |
| 2006/0017957 A1 | 1/2006 | Degott et al. |
| 2006/0017959 A1 | 1/2006 | Downer et al. |
| 2006/0117465 A1 | 6/2006 | Willows et al. |
| 2006/0121181 A1 | 6/2006 | Sleat et al. |
| 2006/0286569 A1 | 12/2006 | Bar-Or et al. |
| 2007/0048761 A1 | 3/2007 | Reep et al. |

FOREIGN PATENT DOCUMENTS

| | | |
|---|---|---|
| EP | 1403333 A1 | 3/2004 |
| GB | WO 87/06383 | 10/1987 |
| GB | 2434570 | 8/2007 |
| RU | 2170064 C1 | 10/2001 |
| SE | WO 97/45539 | 12/1997 |
| WO | WO 9014441 | 11/1990 |
| WO | 9204469 | 3/1992 |
| WO | WO 9506249 | 6/1994 |
| WO | WO 9502702 A1 | 1/1995 |
| WO | 9506249 | 3/1995 |
| WO | WO 9959011 | 11/1999 |
| WO | WO 0055609 | 9/2000 |
| WO | WO 0125002 A1 | 4/2001 |
| WO | WO 0199063 A1 | 12/2001 |
| WO | WO 02057548 A1 | 7/2002 |
| WO | WO 02084617 A1 | 10/2002 |
| WO | 03080931 | 10/2003 |
| WO | WO 03080931 A1 | 10/2003 |
| WO | 2004025562 | 3/2004 |
| WO | WO 2004025582 A1 | 3/2004 |

OTHER PUBLICATIONS

Wollenberger, L.V. Detection of DNA using upconverting phosphor reporter probes.(1997). Proceedings of SPIE-The International Society for Optical Engineering, 2895(Ultrasensitve Biochemical Diagnostics II), 100-111.

Versalift, "Market Growth: the evolution of the aerial lift industry," Oct. 1, 2002. Accessed on web Nov. 10, 2008.

Schultz et al., "Archived or directly swabbed latent fingerprints as a DNA source for STR typing," Forensic Science International, 127 (2002) 128-130.

Zuckermann, et al. "Efficient methods for attachment of thiol specific probes to the 3'-ends of synthetic oligodeoxyribonucleotides." Nucleic Acids Research, vol. 15, pp. 5305-5321 (1987) IRL Press Limited, Oxford, England.

Whitcombe, et al. "Detection of PCR products using self-probing amplicons and fluorescence." Nature Biotechnology, vol. 17, pp. 804-807 (1999), Nature America, Inc., New York.

Nazarenko, et al. "A closed tube format for amplification and detection of DNA based on energy transfer." Nucleic Acids Research, vol. 25, pp. 2516-2521 (1997) Oxford University Press.

Sproat, et al. "The synthesis of protected 5'-mercapto-2', 5'-ddeoxyribonucleoside-3-O-phosphoramidies uses of 5'-mercapto-oligodeoxynbonucleotides." Nucleic Acids Research vol. 15 pp. 4837-4648 (1967) IRL Press Limited, Oxford, England.

Nelson, et al. "Bifunctional oligonucleotide probes synthesized using a novel CPG support are able to detect single base pair mutations" Nucleic Acids Research, vol. 17, pp. 7187-7194 (1989). IRL Press Limited, Oxford, England.

Gupta, et al. "A general method for the synthesis of 3'-sulthydryl and phosphate group containing oligonucleotides" Nucleic Acids Research, vol. 19, pp. 3019-3025 (1991) Oxford University Press, Oxford, England.

Holland, et al. "Detection of specific polymerase chain reaction product by utilizing the 5'[to] 3'exonuclease activity of *Thermus aquatious* DNA polymerase" Proceedings of the National Academy of Sciences, vol. 68, pp. 7276-7280 (1991), National Academy of Sciences, Washington, DC.

Gibson, et al. "A Novel Method for Real Time Quantitative RT-PCR" Genome Research, vol. 6, pp. 995-1001 (1996), Cold Spring Harbor Laboratory Press, Woodbury, NY.

(56) References Cited

OTHER PUBLICATIONS

Agrawal & Tang "Site-specific functionalization of oligodeoxynucleotides for non-radioactive labeling" Tetrahedon Letters, vol. 31, pp. 1543-1546 (1990) Pergamon Press, Great Briton.

Hussein et al. "Molecular Characterization of Cotton Genotypes Using PCR-based Markers." Journal of Applied Sciences Research 3 (10): 1156-1169 (2007).

Jiang et al. "Polyploid forniation created unique aventies for response to selection in Gossypium (cotton)." Proceedings of the National Academy of Sciences, USA, vol. 95, pp. 4419-4424, Apr. 1998.

Lee et al. "The complete chloroplast genome sequence of *Gossypium hirsutum* organization and phylogenetic relationships to other angiosperms" BMC Genomics 761, Mar. 2006.

Ibrahim et al. Complete nucleotide Sequence of the Cotton (*Gossypium barbadense* L.) Chloroplast Genome with a Comparative Analysis of sequence among 9 Disct Plants. Genes and Genetic Systems vol. 61, pp. 311-321.

Van De Rijke, et al. "Up-converting phosphor reporters for nucleic acid microarrays." Nature Biotechnology, vol. 19, pp. 273-276 (2001). Nature Publishing Group, New York.

Corstjens, et al. "Infrared up-converting phosphors for bioassays." IEE Proceedings—Nanobiotechnology, vol. 152, pp. 64-72 (2005). Institution of Engineering and Technology, London.

Heid, et al. "Real Time Quantitative PCR." Genome Research, vol. 6, pp. 986-994 (1996). Cold Spring Harbor Laboratory Press, Woodbury, New York.

Tyagi & Kramer. "Molecular Beacons: probes that Fluoresce upon Hybridization." Nature Biotechnology, vol. 14, pp. 303-308 (1996). Nature Publishing Group, New York.

Lee, et al. "Allelic discrimination by nick-translation PCR with fluorogenic probes." Nucleic Acids Research, vol. 21, pp. 3761-3766 (1993). Oxford University Press, Oxford, England.

Tyagi, et al. "Multicolor molecular beacons for allele discrimination." Nature Biotechnology, vol. 16, pp. 49-53 (1997). Nature Publishing Group, New York.

\* cited by examiner

OPTICAL REPORTER COMPOSITIONS

CROSS REFERENCE

This application is a continuation patent application of U.S. Ser. No. 11/954,030 filed on Dec. 11, 2007, which is a continuation-in-part of patent application Ser. No. 11/437,265 having a filing date of May 19, 2006 which claims the benefit of provisional patent application No. 60/682,976 filed on May 20, 2005; U.S. Ser. No. 11/954,030 is also a continuation-in-part of patent application Ser. No. 10/825,968 having a filing date of Apr. 15, 2004 which claims the benefit of provisional patent application No. 60/463,215 filed on Apr. 16, 2003; Ser. No. 11/954,030 also claims the benefit of provisional patent application 60/874,425 having a filing date of Dec. 12, 2006; Ser. No. 11/954,030 also claims the benefit of provisional patent application Nos. 60/877,875 and 60/877,869 each having a filing date of Dec. 29, 2006; each of these patent applications being hereby incorporated by reference including the six co-filed patent applications having Ser. Nos. 11/954,009; 11/954,030; 11/954,038; 11/954,044; 11/954,051 and 11/954,055 each filed on Dec. 11, 2007; now issued as U.S. Pat. Nos. 8,124,333; 8,372,648; 8,426,216; 8,415,164; 8,415,165 and 8,420,400; respectively.

FIELD

This invention pertains to compositions comprising optical reporters, and more specifically up-converting phosphors (UCP) that are linked to nucleic acids of detectable sequence.

BACKGROUND

Optical reporters such as fluorescent dyes and upconverting phosphors have been used vigorously to detect the presence of biomolecules such as proteins and DNA molecules. Up-converting phosphor particles (UCP) have been encapsulated in transparent polyacrylate micro-carriers which can form covalent bonds with protein sensors via functional groups as described in U.S. Pat. No. 5,132,242. Silylation techniques have also been utilized for binding antibodies to UCPs. Biotin/avidin binding has been utilized to detect biotinylated deoxyribonucleic acid (DNA) by UCP particles with avidin molecules on their surfaces. Hapten/digoxigenin sandwich technology has also been used to indirectly detect the presence of DNA with modified UCP particles.

Heretofore, the covalent binding of UCP particles to DNA molecules of detectable sequence has not been known. Such particles would be useful for labeling and identification of articles and materials and as probes for characterizing DNA. There is accordingly a need for compounds compositions comprising an up-converting phosphor linked to a sequence-able DNA molecule. The present invention satisfies these needs as well as others.

SUMMARY

This invention relates primarily to the compositions which link biomolecules to visual or machine detectable reporters. Reporters can be easily detected by using a high energy light source for excitation, and the location of labeled biomolecules is identified by the presence of a reporter. Nevertheless, after the location of biomolecules, there is often a need to analyze biomolecules further, particularly when the biomolecule is a DNA molecule, by PCR or sequence analysis techniques.

A composition of the formula I:

$$(cOpR)\text{-}[L\text{-}(NA)]_m \qquad \text{I}$$

wherein: m is an integer greater than 1, (cOpR) is a coated optical reporter particle, (NA) is a nucleic acid oligomer of detectable sequence and L is a linking group covalently bound to the coated optical reporter particle and to the nucleic acid oligomer.

The (cOpR) of the composition may comprise an upconverting phosphor (UCP) material biomolecule is a DNA molecule, by PCR or sequence analysis techniques.

In most embodiments, the cOpR of the composition of the invention is coated with silica.

In some embodiments where the compositions are coated with silica, the silica comprises at least one Si—O bond.

The (NA) of the composition may be a single or double stranded DNA molecule having a length of between about 40 base pairs and about 1000 base pairs.

The linker or L of the composition may comprise an alkylene moiety having a first end covalently bound to the coated optical reporter particle and a second end covalently bound to the nucleic acid oligomer.

Where the composition comprises a (UCP), in certain embodiments, the (UCP) is an upconverting phosphor particle of the formula:

$$Y_xYb_yEr_zO_2S; \text{ or}$$

$$Na(Y_xYb_yEr_z)F_4;$$

wherein:
x is from about 0.6 to about 0.95;
y is from about 0.05 to about 0.35; and
z is from about 0.1 to about 0.001.

In other embodiments, the linker L of compositions having the formula of I: $(cOpR)\text{-}[L\text{-}(NA)]_m$, L has the formula:

$$\text{-A-R}^1\text{—B—}$$

where $R^1$ is $C_{2\text{-}8}$alkylene, -A- is a group covalently bonded to the surface of the coated optical reporter and —B— is a group covalently bonded to the 3' or 5' end of the nucleic acid oligomer.

In other embodiments, a composition of the invention has the formula:

$$(UCP)\text{-}[A\text{-}R^1\text{—B-}(DNA)]_m$$

where m is an integer greater than 1; UCP is an upconverting phosphor particle; DNA is a single or double stranded deoxyribonucleic acid oligomer; $R^1$ is $C_{2\text{-}8}$alkylene; -A- is a group capable of covalently bonding to the surface of the upconverting phosphor particle and —B— is a group capable of bonding to the 3' or 5' end of the deoxyribonucleic acid oligomer.

All patents and publications identified herein are incorporated herein by reference in their entirety.

DESCRIPTION

Definitions

Figure 1:
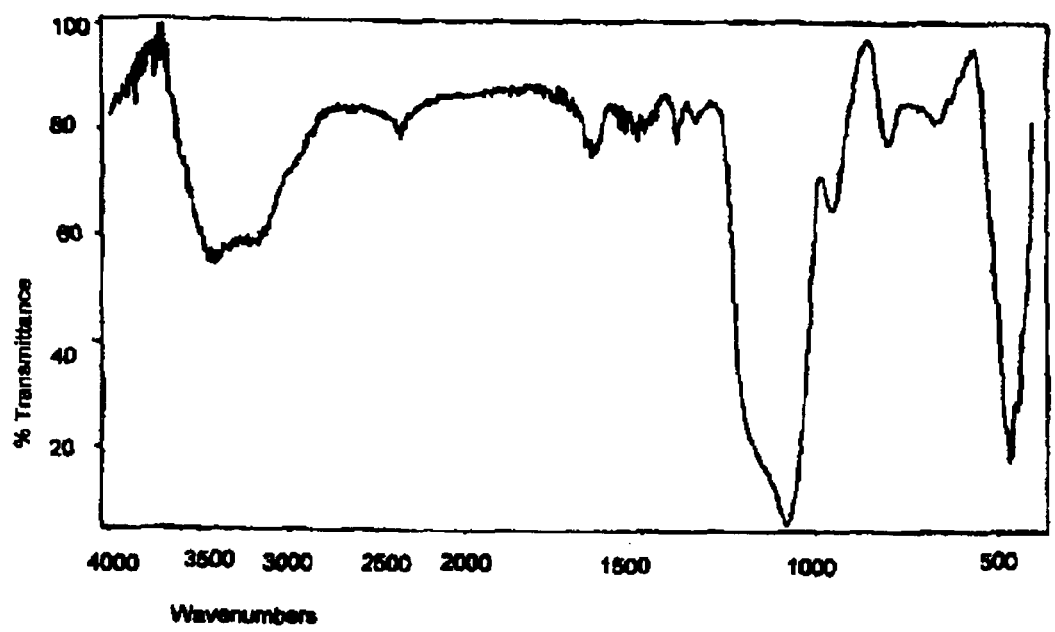
FIG. 1 is an FTIR Spectrum of a silinated coated optical reporter particle in accordance of the methods of the invention.

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl" means a moiety of the formula —R'—R"—R'" where R' is alkylene, R" is —$SO_2$— and R'" is alkyl as defined herein.

"Alkylamino means a moiety of the formula —NR—R' wherein R is hydrogen or alkyl and R' is alkyl as defined herein.

Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

"Arylalkyl" and "Aralkyl", which may be used interchangeably, mean a radical-$R^a R^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —$SO_2$—R wherein R is aryl as defined herein.

"Aryloxy" means a group of the formula —O—R wherein R is aryl as defined herein.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^b R^c$, and —$S(O)_n R^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is O, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof, each optionally substituted.

"Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Urea" or means a group of the formula —NR'—C(O)—NR'R''' wherein R', R" and R''' each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R''' each independently is hydrogen or alkyl.

"Optionally substituted", when used in association with "aryl", phenyl", "heteroaryl" "cycloalkyl" or "heterocyclyl", means an aryl, phenyl, heteroaryl, cycloalkyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR, —SO$_2$R (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Optional" or "optionally" means that the subsequently described event or circumstance may but need not occur, and that the description includes instances where the event or circumstance occurs and instances in which it does not.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The terms "those defined above" and "those defined herein" when referring to a variable incorporates by reference the broad definition of the variable as well as preferred, more preferred and most preferred definitions, if any.

The term "emitting reporter" means a chemical substituent or material that produces, under appropriate excitation conditions, a detectable optical signal. The optical signal produced by an emitting reporter is typically electromagnetic radiation in the near-infrared, visible, or ultraviolet portions of the spectrum. The emitting reporters of the invention are generally up-converting reporters, but can also be for example, fluorescent and colorimetric substituents.

The term "phosphor particle" means a particle or composition comprising at least one type of upconverting phosphor material.

The term "primer" means a nucleotide with a specific nucleotide sequence which is sufficiently complimentary to a particular sequence of a target DNA molecule, such that the primer specifically hybridizes to the target DNA molecule.

The term "probe" refers to a binding component which binds preferentially to one or more targets (e.g., antigenic epitopes, polynucleotide sequences, macromolecular receptors) with an affinity sufficient to permit discrimination of labeled probe bound to target from nonspecifically bound labeled probe (i.e., background).

The term "probe polynucleotide" means a polynucleotide that specifically hybridizes to a predetermined target polynucleotide.

The term "oligomer" refers to a chemical entity that contains a plurality of monomers. As used herein, the terms "oligomer" and "polymer" are used interchangeably. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure.

The term "PCR" refers to polymerase chain reaction. This refers to any technology where a nucleotide is amplified via a temperature cycling techniques in the presence of a nucleotide polymerase, preferably a DNA polymerase. This includes but is not limited to real-time per technology, reverse transcriptase-per, and standard PCR methods.

The term "nucleic acid" means a polymer composed of nucleotides, e.g. deoxyribonucleotides or ribonucleotides, or compounds produced synthetically which can hybridize with naturally occurring nucleic acids in a sequence specific manner analogous to that of two naturally occurring nucleic acids, e.g., can participate in hybridization reactions, i.e., cooperative interactions through Pi electrons stacking and hydrogen bonds, such as Watson-Crick base pairing interactions, Wobble interactions, etc.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "polynucleotide" or "nucleotide" refer to single or double stranded polymer composed of nucleotide monomers of generally greater than 50 nucleotides in length.

The term "monomer" as used herein refers to a chemical entity that can be covalently linked to one or more other such entities to form an oligomer. Examples of "monomers" include nucleotides, amino acids, saccharides, peptides, and the like. The term nucleotide means The term "linker" means a compound or a composition which covalently links a biomolecule to the surface of a coated emitting reporter. For example, but not limited to a silyinated coated upconverting phosphor particle linked to a DNA molecule.

The term "identifiable sequence" or "detectable sequence" means a nucleotide sequence which can by detected by hybridization and/or PCR technology by a primer or probe designed for specific interaction with the target nucleotide sequence to be identified. The interaction of the target nucleotide sequence with the specific probe or primer can be detected by optical and/or visual means to determine the presence of the target nucleotide sequence.

Nomenclature and Structures

In general, the nomenclature used in this application is based on AUTONOM™ v.4.0, a Beilstein Institute computerized system for the generation of IUPAC systematic nomenclature. Chemical structures shown herein were prepared using ISIS® version 2.5. Any open valency appearing on a carbon, oxygen sulfur or nitrogen atom in the structures herein indicates the presence of a hydrogen atom unless indicated otherwise. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure.

Compounds of the Invention

The invention provides compounds of the formula I:

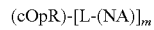

(cOpR)-[L-(NA)]$_m$ wherein:

m is an integer greater than 1;

(cOpR) is a coated optical reporter particle;

(NA) is a nucleic acid oligomer of detectable sequence; and

L is a linking group covalently bound to the coated optical reporter particle and to the nucleic acid oligomer.

While formula I specifically relates to linking nucleic acid oligomers or nucleotides to the surface of the coated optical reporter particle, it should be understood to the those skilled in the art that other biomolecules besides nucleotides can be linked to L. Such biomolecules include but are not limited to peptides, proteins, antibodies, enzymes, DNA binding proteins and the like. These biomolecules, may be modified to include lipids, carbohydrates, fluorescent and/or upconverting phosphor molecules or other detectable compounds or markers.

In most embodiments, NA is a DNA oligomer. The DNA oligomer may be either single stranded DNA or double stranded DNA. In certain embodiments NA may be comprise cDNA, RNA, STR (single tandem repeat) or SNP (single nucleotide polymorphism). NA oligomers of the compositions of the invention may also be modified to comprise at least one dUTP nucleic acid or at least one nucleic acid within the oligomer which has been modified to contain a detectable marker.

In many embodiments NA is a DNA oligomer having a length of between about 40 base pairs and about 1000 base pairs (per strand).

In other embodiments the DNA has a length of between about 80 and 500 base pairs (per strand).

In yet other embodiments the DNA has a length of between about 100 to about 250 base pairs (per strand).

The DNA used with the invention may be natural or synthetically produced. All or a portion of the DNA may comprise an identifiable sequence.

In certain embodiments of formula I, the coated optical reporter comprises a visible or infrared detectable light emitting material selected from the group consisting of a fluorescent dye, an upconverting phosphor, a ceramic powder, or a quantum dot material. In most embodiments where the cOpR comprises a visible or infrared detectable light emitting material, the light emitting materials are excitable by UV, visible or an infrared light source.

In some embodiments, rare earth-doped ceramic particles are used as phosphor particles. Phosphor particles may be detected by any suitable method, including but not limited to up-converting phosphor technology (UPT), in which up-converting phosphors transfer lower energy infrared (IR) radiation into higher-energy visible light. Although an understanding of the mechanism is not necessary to practice the present invention and the present invention is not limited to any particular mechanism of action, in some embodiments the UPT up-converts infrared light to visible light by multi-photon absorption and subsequent emission of dopant-dependant phosphorescence (See, e.g., U.S. Pat. No. 6,399,397; van De Rijke, et al., Nature Biotechnol. 19(3):273-6 (2001); Corstjens, et al., IEE Proc. Nanobiotechnol. 152(2):64 (2005), each incorporated by reference herein in its entirety.

In many embodiments, the phosphor nanoparticles may be of the formula A $$(Y_xRE^1_yRE^2_z)_2O_3 \quad A$$

wherein:
RE$^1$ and RE$^2$ each is a different rare earth element;
x is from about 0.6 to about 0.95;
y is from 0 to about 0.35; and
z is from 0 0.1 to about 0.001;
provided that y and z are not simultaneously equal to 0.

The rare earth elements RE$^1$ and RE$^2$ may each independently be selected from Ytterbium, Erbium, Holmium, Thulium, or Terbium.

In many embodiments RE$^1$ is Ytterbium.

In many embodiments RE$^2$ is Erbium.

The up-converting particles utilized in the methods of the invention may be spherical, non-agglomerated, non-porous particles with an average size of 40-60 nm. In general, particle sizes may range from about 10 nm to about 5 um in size. Such up-converting phosphor nanopowders such as doped yttrium oxide and yttrium oxysulfide are commercially available and may be obtained from such as Nanocerox, Inc., of Ann Arbor, Mich.

Suitable examples of up-converting phosphors are compounds of rare earths or elements from the group IIIB such as: Na-yttrium fluoride, lanthanum fluoride, lanthanum oxysulphide, yttrium oxysulphide, yttrium fluoride, yttrium gallate, gadolinium fluoride, barium-yttrium fluorides, gadolinium oxysulphide as well as compounds of the above type doped with activator pairs such as ytterbium/erbium, ytterbium/thulium or ytterbium/holmium. Other suitable up-converting phosphors include chelate compounds of erbium, neodymium, thulium, holmium and praseodymium.

The following compositions are merely illustrative of some of the up-converting phosphor containing compositions that can be synthesized by the synthetic reaction schemes of the methods of the present invention. Various modifications to these synthetic reaction schemes can be made and will be suggested to one skilled in the art having referred to the disclosure contained in this application.

TABLE I

Upconverting Phosphor Compositions

| Phosphor Material | Absorber Ion | Emitter Ion |
|---|---|---|
| Oxysulfides (O$_2$S) | | |
| Y$_2$O$_2$S | Ytterbium | Erbium |
| Gd$_2$O$_2$S | Ytterbium | Erbium |
| La$_2$O$_2$S | Ytterbium | Holmium |
| Oxyhalides (OX$_y$) | | |
| YOF | Ytterbium | Thulium |
| Y$_3$OCl$_7$ | Ytterbium | Terbium |
| Fluorides (F$_x$) | | |
| YF$_3$ | Ytterbium | |
| GdF$_3$ | Ytterbium | Erbium |
| LaF$_3$ | Ytterbium | Erbium |
| NaYF$_3$ | Ytterbium | Holmium |
| BaYF$_5$ | Ytterbium | Thulium |
| BaY$_2$F$_8$ | Ytterbium | Thulium |
| Gallates (Ga$_x$O$_y$) | | |
| YGaO$_3$ | Ytterbium | Erbium |
| Y$_3$Ga$_5$O$_{12}$ | Ytterbium | Erbium |
| Silicates (Si$_x$O$_y$) | | |
| YSi$_2$O$_5$ | Ytterbium | Holmium |
| YSi$_3$O$_7$ | Ytterbium | Thulium |

In certain embodiments the coated optical reporter may also comprise at least one electromagnetic emitting material. An electromagnetic emitting material as part of the composition of the invention, allows for the composition to be detected by various methods and devices. Where the electromagnetic emitting material is detectable by mechanical devices which provide at least one source selected from the group consisting of an infrared radiation source, magnetic field source or electromagnetic pulse. This electromagnetic emitting material may be in conjunction with at least one light emitting material, such as an upconverting phosphor.

When the compositions of the invention comprise UCPs, the upconverting phosphor material/particle in certain embodiments have the formula B $$Y_xYb_yEr_zO_2S \quad B$$

wherein:
x is from about 0.6 to about 0.95;
y is from about 0.05 to about 0.35; and
z is from about 0.1 to about 0.001.

In other embodiments, the upconverting phosphor particle may be of the formula C:

$$Na(Y_xYb_yEr_z)F_4 \quad C$$

wherein
x is from about 0.6 to about 0.95
y is from about 0.05 to about 0.35; and
z is from about 0.1 to about 0.001.

In certain embodiments of formula I, L comprises an alkylene moiety having a first end covalently bound to the coated optical reporter particle (cOpR) and a second end covalently bound to the nucleic acid oligomer (NA).

In many embodiments of formula I, L is of the formula D:

$$-A-R^1-B-\qquad\qquad D$$

wherein:

$R^1$ is $C_{2-8}$alkylene;

-A- is a group covalently bonded to the surface of the coated optical reporter; and —B— is a group covalently bonded to the 3' or 5' end of the nucleic acid oligomer.

In certain embodiments of formula D, —$R^1$— is —$(CH_2)_n$— and n is from 2 to 8.

In certain embodiments of formula D, —B— is:

—S—;

—O—;

—$NR^a$—;

—S—$(CH_2)_p$—;

—O—$(CH_2)_p$—;

—$NR^a$—$(CH_2)_p$—;

—S—$(CH_2)_q$—C(O)—$NR^a$—$(CH_2)_p$—;

—O—$(CH_2)_q$—C(O)—$NR^a$—$(CH_2)_p$—;

—$NR^a$—$(CH_2)_q$—C(O)—$NR^a$—$(CH_2)_p$—;

—S—C(O)—$(CH_2)_r$—C(O)—$NR^a$—$(CH_2)_p$—;

—O—C(O)—$(CH_2)_r$—C(O)—$NR^a$—$(CH_2)_p$—; or

—$NR^a$—C(O)—$(CH_2)_r$—C(O)—$NR^a$—$(CH_2)_p$—;

wherein:

p is from 2 to 8;

q is from 1 to 8;

r is from 2 to 8; and each $R^a$ is independently hydrogen or a $C_{1-6}$alkyl.

In certain embodiments of formula D, —B— is:

—S—$(CH_2)_q$—C(O)—$NR^a$—$(CH_2)_p$ or

—$NR^a$—C(O)—$(CH_2)_r$—C(O)—$NR^a$—$(CH_2)_p$—;

wherein:

p is from 2 to 8;

q is from 1 to 8;

r is from 2 to 8; and each $R^a$ is independently hydrogen or a $C_{1-6}$alkyl.

In other embodiments of formula D, —B— is:

—S—$(CH_2)_q$—C(O)—$NR^a$—$(CH_2)_p$ or

—$NR^a$—C(O)—$(CH_2)_r$—C(O)—$NR^2$—$(CH_2)_p$—;

wherein:

p is from 2 to 6;

q is from 1 to 3; and r is 2 or 3.

In other embodiments of formula D, —B— is

—S—$CH_2$—C(O)—NH—$(CH_2)_6$— or

—NH—C(O)—$(CH_2)_3$—C(O)—NH—$(CH_2)_6$—.

In certain embodiments of formula D, -A- is —O—.

In many embodiments of formula I, the coated optical reporter (cOpR) is coated with silica. Usually when the coated optical reporter comprises a coating of silica, the silica comprises at least one Si—O bond.

The value of m in formula I will vary according to the surface area of the coated optical reporter and the number of functional groups on the optical reporter surface cable of bonding to -L-. The value of m is always greater than one, and usually greater than 10. Preferably m is greater than 100, and in many embodiments m is greater than $10^3$. In many embodiments m may be, for example, between about 10 and about $10^9$. In certain embodiments m may be from about 100 to about $10^8$. In some embodiments m may be from about $10^3$ to about $10^7$.

In certain embodiments the compositions of the invention are of the formula II:

$$(UCP)\text{-}[A\text{-}R^1-X-R^2-C(O)-NR^a-R^3\text{-}(DNA)]_m\qquad II$$

wherein:

m is an integer greater than 1;

UCP is an upconverting phosphor particle;

DNA is a single or double stranded deoxyribonucleic acid oligomer;

-A- is a group capable of covalently bonding to the surface of the

Upconverting phosphor particle;

$R^1$ is $C_{2-8}$alkylene, $R^2$ is $C_{1-8}$alkylene or —C(O)—$C_{1-8}$alkylene-;

—X— is —O—, —S— or —$NR^a$—;

$R^3$ is $C_{2-8}$alkylene; and $R^a$ is hydrogen or $C_{1-6}$alkyl.

In certain embodiments of the invention, the subject composition may be of formula III:

$$(UCP)-[O-R^1-X-R^2-C(O)-NH-R^3\text{-}DNA]_m\qquad III$$

wherein m, $R^1$, $R^2$, $R^3$, UCP and DNA are as defined herein.

In certain embodiments of the invention, $R^1$ is $C_{2-6}$alkylene.

In certain embodiments of the invention, $R^2$ is $C_{1-6}$alkylene.

In certain embodiments of the invention, $R^3$ is $C_{2-6}$alkylene.

In certain embodiments of the invention, $R^2$ is —C(O)—$C_{2-6}$alkylene-.

In certain embodiments of the invention, $R^1$ is —$(CH_2)_s$— wherein s is from 2 to 6. In some embodiments s is 3.

In certain embodiments of the invention, $R^2$ is —$(CH_2)_t$— wherein t is from 1 to 6. In some embodiments t is 1.

In certain embodiments of the invention, $R^2$ is —C(O)—$(CH_2)_u$— wherein u is from 1 to 6. In some embodiments u is 2 or 3, preferably 2.

In certain embodiments of the invention, $R^3$ is —$(CH_2)_v$— wherein v is from 2 to 6. In some embodiments v is 6.

In certain embodiments of the invention, the subject composition may be of formula IV:

$$(UCP)-[O-(CH_2)_s-S-(CH_2)_t-C(O)-NH-(CH_2)_v\text{-}(DNA)]_m\qquad IV$$

wherein:

s is from 2 to 6;

v is from 2 to 6;

t is from 1 to 3; and m, UCP and DNA are as defined herein.

In certain embodiments of the invention, the compositions may be of formula V:

$$(UCP)-[O-(CH_2)_s-NH-C(O)-(CH_2)_u-C(O)-NH-(CH_2)_v\text{-}(DNA)]_m\qquad V$$

wherein:
s is from 2 to 6;
v is from 2 to 6;
u is 2 or 3; and
m, UCP and DNA are as defined herein.

In certain embodiments of the invention, the compositions may be of formula VI:

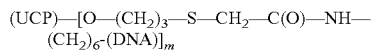
(UCP)—[O—(CH$_2$)$_3$—S—CH$_2$—C(O)—NH—(CH$_2$)$_6$-(DNA)]$_m$      VI wherein m, UCP and DNA are as defined herein.

In certain embodiments of the invention, the compositions may be of formula VII:

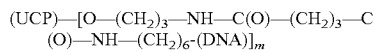
(UCP)—[O—(CH$_2$)$_3$—NH—C(O)—(CH$_2$)$_3$—C(O)—NH—(CH$_2$)$_6$-(DNA)]$_m$      VII wherein m, UCP and DNA are as defined herein.

Synthesis

Nucleotide-labeled optical reporters in accordance with the invention can be made by a variety of methods, including those depicted in the illustrative synthetic reaction schemes shown and described below.

Reagents and solvents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The starting materials and some of the intermediates of the synthetic reaction schemes can be isolated and purified if desired using conventional techniques, including but not limited to, filtration, distillation, crystallization, chromatography, and the like.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare certain compositions of the invention, wherein R is lower alkyl and may be the same or different in each occurrence, $R^d$ is hydrogen or lower alkyl, Y is a leaving group, Ag is an activating group, and m, X, $R^a$, $R^1$, $R^2$ and $R^3$ are as defined herein

SCHEME A

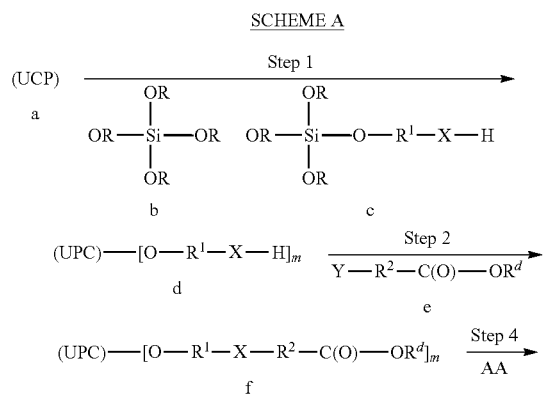

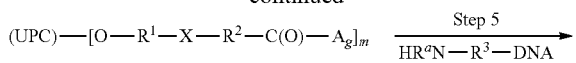

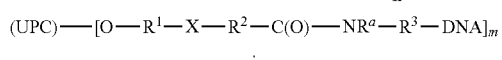

In step 1 of Scheme A, UCP particles a are treated or reacted with a mixture of alkoxysilicate reagents b and c, to form a functionalized UCP particles d. In many embodiments R may be ethyl, such that reagent a is tetraethyl orthosilicate. The ratio of reagents a and b may be varied to vary the value m. In certain embodiments $R^1$ may be —(CH$_2$)$_3$— and —XH may be —SH or —NR$^a$H wherein $R^a$ is hydrogen or lower alky.

In step 2, functionalized particles d are reacted with compound e to afford carboxylate ester-functionalized UCPs f. Y may be halo, mesyl, tosyl, or other suitable leaving groups. In certain embodiments wherein $R^2$ is —C(O)—C$_{1-8}$alkylene-, reagent e may be replaced with a cyclic anhydride such as succinic anhydride, glutaric anhydride, oxetane 2,3-dione, or like anhydride.

The functionalized UCPs f are activated in step 4 by treating UCPs f with an activating agent AA to form functionalized activated UCPs g. The activating agent in many embodiments may be N-hydroxy-succinimide or N-bromo-succinimide such that the group OR in particles f is replaced by a succimido activating group. Other possible activating groups include but are not limited to Nitrophenyl ester.

In step 5 the activated particles are reacted with DNA reagent h to form DNA-labeled UCPs i. The DNA reagent h may comprise, for example, a single stranded DNA oligomer of known sequence having an aminoalkyl group at the 3' or 5' end that is capable of amide coupling with the activated carboxy functional groups on particles h. Various amide coupling techniques may thus be used in step 4, including carbodiimide-based amide couplings. The i of step 4 are a composition of formula I in accordance with the invention.

Many variations on the procedure of Scheme A are possible and will suggest themselves to those skilled in the art. Specific details for producing compositions of the invention are described in the Examples section below.

Utility

The methods of the invention are useful in producing compounds comprising biomolecules such as dsDNA, ssDNA, STR, SNP's as well a peptides and proteins.

The compounds of the invention are usable as authentication markers for various articles. For example, the compounds of the invention can be placed in or on such articles as clothing, paintings, documents, medicines, industrial solutions, computer components, explosives and the like. The compounds produced can also be utilized in micro array technology, as well as protein expression, genomic identification and other technologies utilizing DNA hybridization techniques.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees Celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples.

Up-converting phosphor nanopowder (doped yttrium oxide and yttrium oxysulfide upconverting particles) were obtained from Nanocerox, Inc., Ann Arbor, Mich.

ABBREVIATIONS

UCP Up converting phosphor
UTP Up converting phosphor technology
OpR optical reporter particle
cOpR coated optical reporter particle
TEOS tetraethoxysilane, tetraethyl orthosilicate; ethyl silicate; silicic acid, tetraethyl ester; silicon ethoxide
MOS methyl oxysilane
EOS ethyl oxysilane
POS propyl oxysiline
NHS N-Hydroxsuccinimde
IOA Iodoacetamide
DIPCI Diisopropylcarbodiimide
DBU 1,8-diazabicyclo[5.4.0]undec-7-ene
DCM dichloromethane/methylene chloride
DIPEA diisopropyl ethylamine
DME 1,2-dimethoxyethane (glyme)
DMF N,N-dimethylformamide
DMAP 4-dimethylaminopyridine
ECDI 1-ethyl-3-(3'-dimethylaminopropyl)carbodiimide
EtOAc ethyl acetate
EtOH ethanol
GC Gas Chromatography
HMPA hexamethylphosphoramide
HOBt N-Hydroxybenzotriazole
hplc high performance liquid chromatography
mCPBA m-chloroperbenzoic acid
MeCN acetonitrile
NMP N-methylpyrrolidinone
TEA triethylamine
THF tetrahydrofuran
LDA lithium diisopropylamine
TLC thin layer chromatography Example 1

Doped Yttrium Oxysulfide with Oxypropylsulfanylacetamide-Linked DNA

The synthetic procedure of this Example is shown below in Scheme B.

SCHEME B

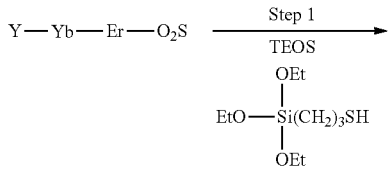

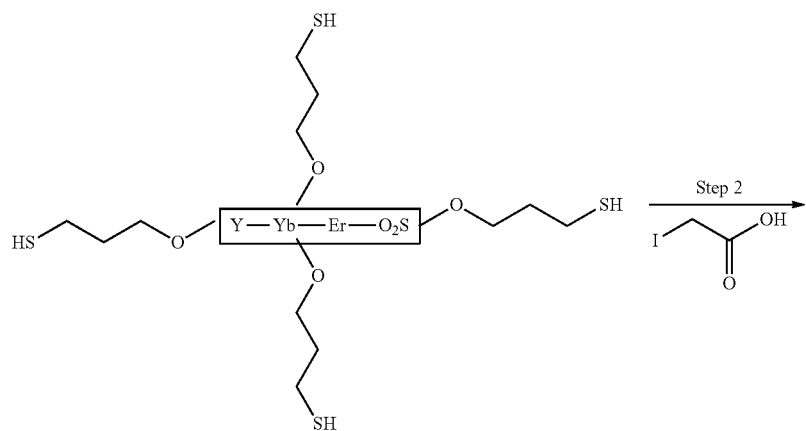

-continued
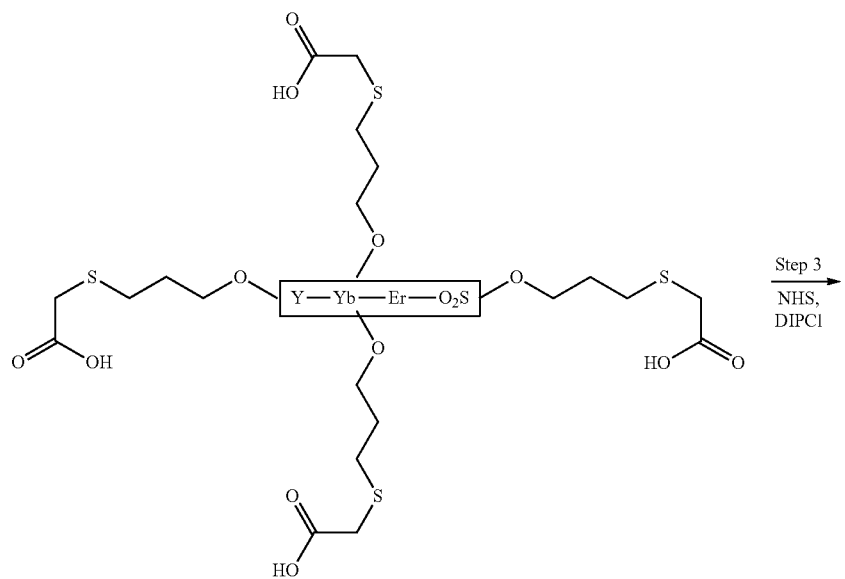
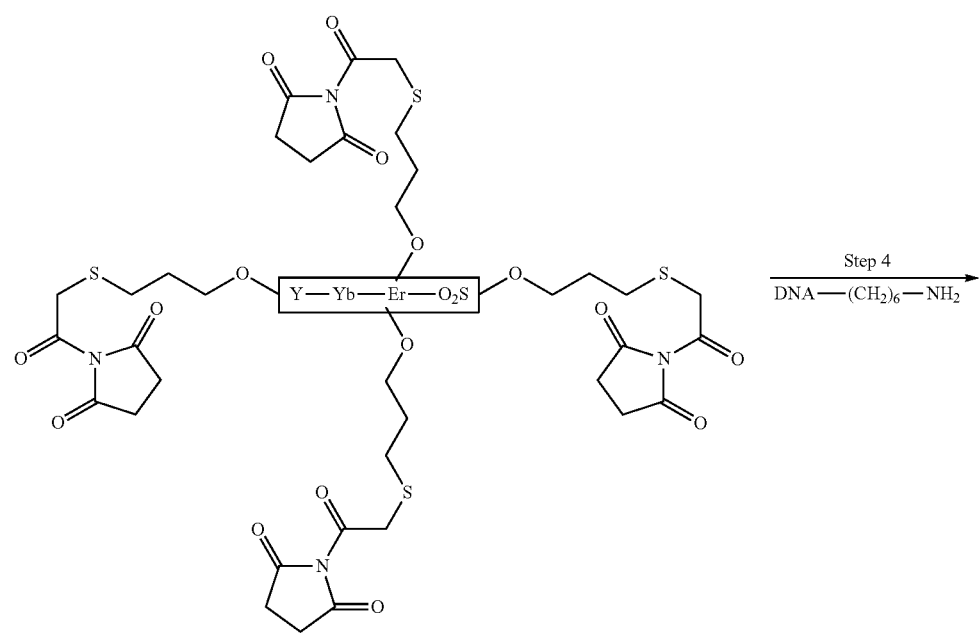

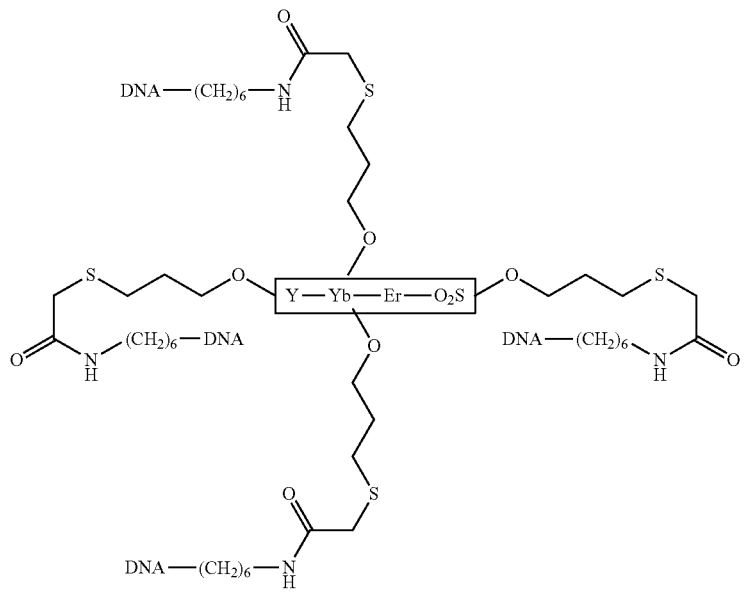

The method utilized in this example generally involved initially coating the upconverting phosphor particles with tetraethyl orthosilicate with ammonium hydroxide present as a catalyst followed by hydrolysis with thiotriethoxysilane.[1] The coated particles were then treated with iodoacetic acid under basic conditions. The particles now modified with carboxylic acid groups were activated using N-hydroxysuccinimide (NHS) and diisopropylcarbodiimide (DIPCI). Subsequently after activation, amino $C_6$ DNA was added to the mixture, for DNA attachment to the phosphor coated particles. The particles were isolated and washed extensively with copious amounts of water removing unreacted amino $C_6$ DNA and other reagents. The isolated phosphor particles were then evaluated by PCR to determine the detectable presence of the covalently attached DNA bound to the coated nanophosphor particles.

General

Doped yttrium oxide and yttrium oxysulfide upconverting particles were from Nanocerex (Ann Arbor, Mich.). Tetraethoxysilane was 99+% and 3-aminopropyltriethoxysilane was 99% both from Aldrich. 3-Mercaptopropyltriethoxysilane was 95% from Gelest and was lot #3C-2709. N-Hydroxsuccinimde, glutaric anhydride and iodoacetic acid were from Aldrich. The 5' C6 amino modified DNA was a 180-mer with a molecular weight of 55,867 and was obtained from Integrated DNA Technologies. In general, the 5' amino modified DNA molecule is produced by modifying the 5' end of the last sugar molecule of the DNA chain via an OH and ultimately forms an ether linkage forming [sugar]-O—$(CH_2)_6$—$NH_2$. The concentration of the modified DNA was 1 nM. The 5' amino linker portion of the modified DNA can range from two carbons to about 18 carbons in length. 2-Propanol was HPLC grade from Aldrich or Fisher. The ultrasonic cleaning bath was a Heat Systems-Ultrasonics.

Particles were isolated by centrifuging using screw capped 50 mL polypropylene Falcon tubes and a ICE Model HN—S benchtop centrifuge.

Step 1 Mercaptopropyl Functionalized Silylated Yttrium Oxysulfide Particles:

Yttrium oxysulfide upconverting particles (100 mg) were suspended in 100 mL of de-aerated 2-propanol and sonicated under nitrogen for 75 min. De-aerated water (7.5 mL) was added and sonication continued for 5 min. Concentrated ammonium hydroxide (9 mL) was added and sonication continued a final 10 min. The milky white suspension was placed in an oil bath at 40±2° and stirred magnetically under nitrogen for 10 min. Tetraethoxysilane (0.3 mL) was added the mixture stirred for 2 hr. 3-Mercaptopropyltriethoxysilane (0.3 mL) was added and stirring continued for 2.5 hr. The particles were isolated by centrifuging and washed with 30 mL of 2-propanol. They were then washed with 20 mL of 5% acetic acid in 2-propanol and finally with 20 mL of 2-propanol. The particles were dried under vacuum (1.0 mm) at room temperature overnight.

Step 2 Reaction of Thiol Functionalized Yttrium Oxysulfide Particles with Iodoacetic Acid:

Iodoacetic acid (50 mg, 0.27 mmol) was dissolved in 20 mL of 0.2M aqueous sodium bicarbonate. The pH of the solution was about 8.4 (narrow range pH paper). The thiol functionalized particles (~100 mg) from step 1 were added and the mixture sonicated in the dark under nitrogen for 10 hr. An additional 50 mg of iodoacetic acid was added and sonication continued overnight. During this time the bath temperature rose to 40°. The particles were isolated by centrifuging and washed with 10 mL of water. They were then sonicated with 10 mL of 10% aqueous acetic acid. The particles were isolated by centrifuging, washed with 10 mL of water and vacuum dried overnight. The particles were examined by transmission FTIR (KBr disk). There was a strong Si—O absorption at 1100 $cm^{-1}$.

Step 3 Activation of the Carboxy Yttrium Oxysulfide Particles with N-Hydroxysuccinimide:

The carboxy yttrium oxysulfide particles from step 2 (~100 mg) were suspended in 10 mL of 2-propanol and sonicated for 90 min. N-Hydroxysuccinimide (58 mg, 0.5 mmol) was added and sonication continued for 5 min. The suspension was transferred to a 20 mL scintillation vial and diisopropylcarbodiimide (80 uL, 0.5 mmol) added with stirring. The mixture was stirred at room temperature (25°) overnight (15 hr). The particles were isolated by centrifuging then washed by centrifuging with 10 mL of 2-propanol and then twice with 5 mL of the same solvent. They were finally dried in vacuum at room temperature for about 5 min and used immediately in the next step for reaction with DNA.

Step 4 Treatment of the Activated Particles with Amino Modified DNA:

The activated yttrium oxysulfide particles from step 3 (~50 mg) were suspended in 5 mL of 50 mM borate buffer (pH 8.45) using a Vortex mixer. The amino functionalized long chain DNA (2 nmole) in 50 uL of water was added and the mixture was stirred magnetically at room temperature for 24 hr. The particles were isolated by centrifuging and washed with 5 mL of the borate buffer and then with twice with 5 mL of water. They were suspended in 2 mL of water and stored at 5°.

Example 1

Alternate Procedure

Step 1 Mercaptopropyl Functionalized Silylated Yttrium Oxide Particles:

Yttrium oxide upconverting particles (100 mg) were suspended in 100 mL of de-aerated 2-propanol and sonicated under nitrogen for 90 min. De-aerated water (7.5 mL) was added and sonication continued for 5 min. Concentrated ammonium hydroxide (9 mL) was added and sonication continued a final 10 min. The milky white suspension was placed in an oil bath at 40±2° and stirred magnetically under nitrogen for 10 min. Tetraethoxysilane (0.3 mL) was added and the mixture stirred for 2 hr. 3-Mercaptopropyltriethoxysilane (0.3 mL) was added and stirring continued for 2.5 hr. The particles were isolated by centrifuging and washed with 40 mL of 2-propanol. They were then washed with 20 mL of 5% acetic acid in 2-propanol and finally with 20 mL of 2-propanol. The particles were dried under vacuum (1.0 mm) at room temperature (20° overnight.

Step 2 Reaction of Thiol Functionalized Yttrium Oxide Particles with Iodoacetic Acid:

The thiol functionalized yttrium oxide particles from step 2 (~90 mg) were suspended in 20 mL of 0.2M de-aerated aqueous sodium bicarbonate and the mixture sonicated in the dark under nitrogen for 15 min. The particles were transferred to a flask and iodoacetic acid (50 mg, 0.27 mmol) added. The suspension was stirred magnetically at 40±2° under nitrogen for 5 hr. An additional 50 mg of iodoacetic acid was added and stirring continued overnight (14 hr). The particles were isolated by centrifuging and washed with 10 mL of water. They were then sonicated with 10 mL of 10% aqueous acetic acid for 10 min. The particles were isolated by centrifuging, washed with 10 mL of water and vacuum dried overnight. The particles were examined by transmission FTIR (KBr disk). There was a strong Si—O absorption at 1100 cm$^{-1}$.

Step 3 Activation of the Carboxy Yttrium Oxide Particles with N-Hydroxysuccinimide:

The carboxy yttrium oxide particles of step 2 (~80 mg) were suspended in 10 mL of 2-propanol and sonicated for 60 min. N-Hydroxysuccinimide (58 mg, 0.5 mmol) was added and sonication continued for 10 min. The suspension was transferred to a 20 mL scintillation vial and diisopropylcarbodiimide (80 uL, 0.5 mmol) added with stirring. The mixture was stirred at room temperature (~25°) overnight (18 hr). The particles were isolated by centrifuging then washed by centrifuging with 10 mL of 2-propanol and then with 2×5 mL of the same solvent. They were finally dried in vacuum at room temperature for about 5 min and used immediately in the next step for reaction with DNA.

Step 4 Treatment of the Activated Yttrium Oxide Particles with Amino Modified DNA:

The activated particles from step 3 (~80 mg) were suspended in 10 mL of 50 mM borate buffer (pH 8.45) using a Vortex mixer. The amino functionalized long chain DNA (1 nmole) in 50 uL of water was added and the mixture and stirred magnetically at room temperature for 22 hr. The DNA linker in this example was 6 carbons long, and the single stranded DNA oligomer comprised 180 bases. The particles were isolated by centrifuging and washed with 10 mL of the borate buffer and then with twice with 10 mL of water. They were suspended in 2 mL of water and stored at 5°.

Example 2

Doped Yttrium Oxysulfide with (oxy-propylamino)-acetic acid 5-amino-4-oxo-pentyl ester-linked DNA The synthetic procedure of this example is shown below in Scheme C.

SCHEME C

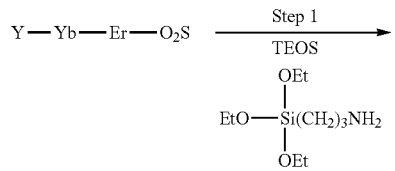

-continued
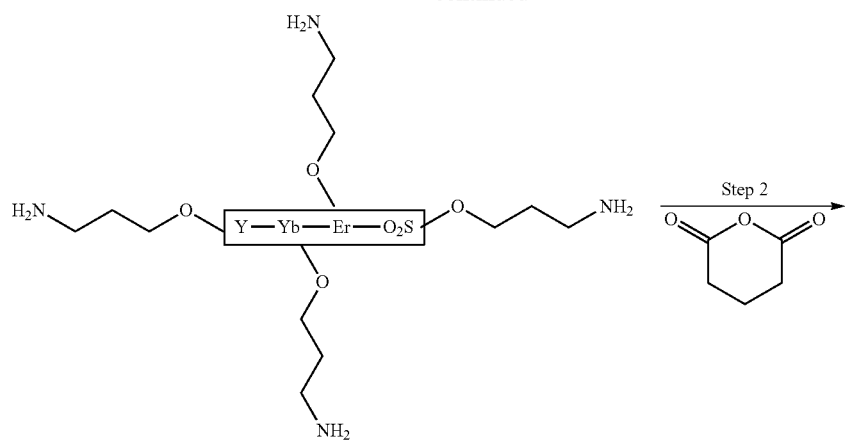
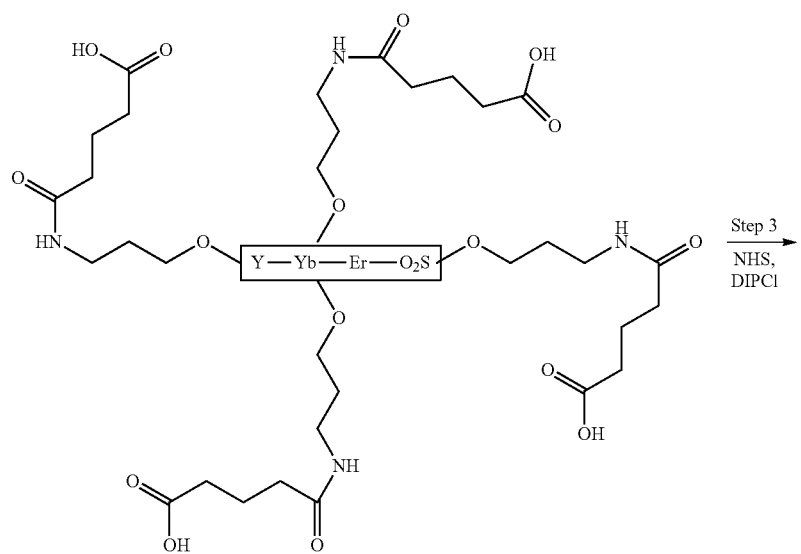
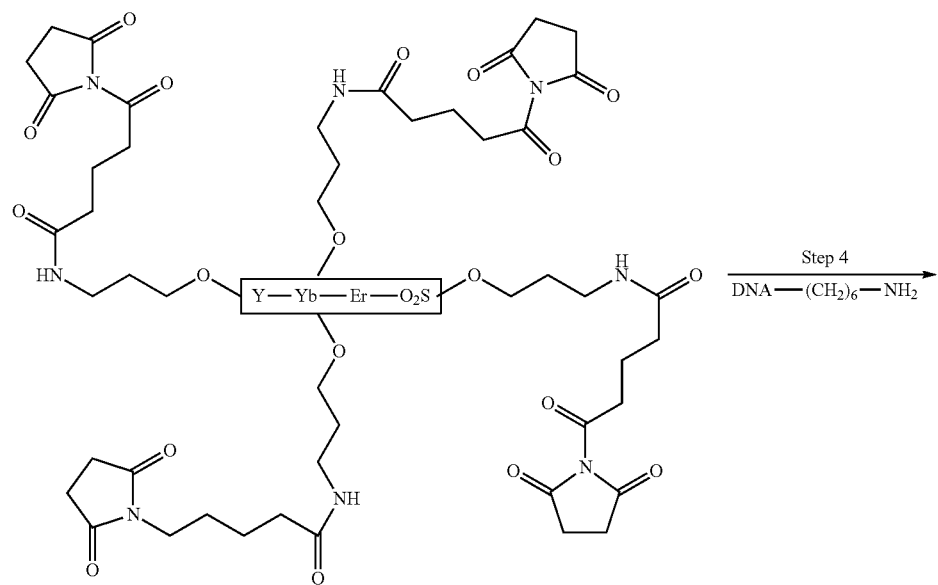

-continued

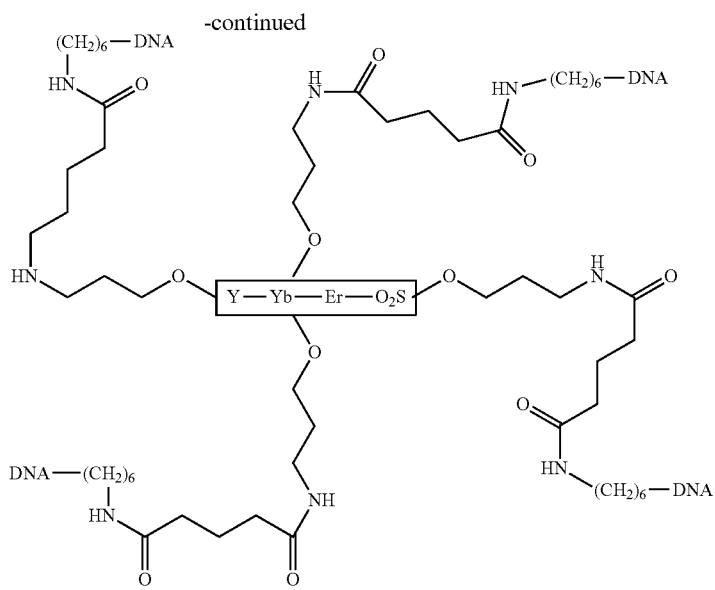

The method utilized in this example generally involved initially coating the upconverting phosphor particles with tetraethyl orthosilicate with ammonium hydroxide present as a catalyst followed by hydrolysis with thiotriethoxysilane. The coated particles were then treated with iodoacetic acid under basic conditions. The particles now modified with carboxylic acid groups were activated using N-hydroxysuccinimide (NHS) and diisopropylcarbodiimide (DIPCI). Subsequently after activation, amino $C_6$ DNA was added to the mixture, for DNA attachment to the phosphor coated particles. The particles were isolated and washed extensively with copious amounts of water removing unreacted amino $C_6$ DNA and other reagents. The isolated phosphor particles were then evaluated by PCR to determine the detectable presence of the covalently attached DNA bound to the coated nanophosphor particles.

Step 1 Aminopropyl Functionalized Silylated Yttrium Oxysulfide Particles:

Yttrium oxysulfide upconverting particles (100 mg) were suspended in 100 mL of de-aerated 2-propanol and sonicated under nitrogen for 75 min. De-aerated water (7.5 mL) was added and sonication continued for 10 min. Concentrated ammonium hydroxide (9 mL) was added and sonication continued a final 10 min. The milky white suspension was placed in an oil bath at 40±2° and stirred magnetically under nitrogen for 10 min. Tetraethoxysilane (0.3 mL) was added and the mixture stirred for 2 hr. 3-Aminopropyltriethoxysilane (0.3 mL) was added and stirring continued for 2.7 hr. The particles were isolated by centrifuging and washed three times with 20 mL of 2-propanol. The particles were dried under vacuum (1.0 mm) at room temperature (30°) overnight. Analysis by transmission FTIR (KBr disk) showed a strong Si—O absorption at 1100 cm$^{-1}$. FIG. 1 is an FTIR spectrum of yttrium oxysulfide upconverting particles after treatment of with TEOS for 2 hours, followed by 3-aminopropyl triethoxysilane for 12 hours. FIG. 1 shows the strong absorption of the Si—O bond at 1100 cm$^{-1}$, demonstrated the silination of the UCP particles.

Step 2 Reaction of the Amino Functionalized Yttrium Oxysulfide Particles with Glutaric Anhydride:

Glutaric anhydride (0.34 g, 3.0 mmol) was dissolved in 13 mL of 2-propanol (minimum volume needed at room temperature) (30°). The solution was added to the amino functionalized yttrium oxysulfide particles (90 mg) and the mixture sonicated for an hour at 30-35°. The suspension was transferred to a flask and stirred magnetically at 40° for 24 hr. The particles were isolated by centrifuging and washed three times with 10 mL of 2-propanol then dried under vacuum at room temperature (26°) overnight.

Step 3 Activation of the Carboxy Yttrium Oxysulfide Particles with N-Hydroxysuccinimide:

The previous carboxy yttrium oxysulfide particles (~80 mg) were suspended in 10 mL of 2-propanol and sonicated for 60 min. N-Hydroxysuccinimide (58 mg, 0.5 mmol) was added and sonication continued for 5 min. The suspension was transferred to a 20 mL scintillation vial and diisopropylcarbodiimide (80 uL, 0.5 mmol) added with stirring. The mixture was stirred at room temperature (~23°) overnight (21 hr). The particles were isolated by centrifuging then washed by centrifuging with 10 mL of 2-propanol and then twice with 5 mL of the same solvent. They were finally dried in vacuum at room temperature for about 5 min and used immediately in the next step for reaction with DNA.

Step 4 Treatment of the Activated Yttrium Oxysulfide Particles with Amino Modified DNA:

The activated particles (~80 mg) were suspended in 10 mL of 50 mM borate buffer (pH 8.45) using a Vortex mixer. The amino functionalized long chain DNA (1 nmole) in 50 uL of water was added and the mixture sonicated for a few minutes. The DNA linker in this example was 6 carbons long, and the single stranded DNA oligomer comprised 180 bases. It was transferred to a 20 mL scintillation vial and stirred magnetically at room temperature (22°) for 20 hr. The particles were isolated by centrifuging and washed with 10 mL of the borate buffer and then three times with 10 mL of water. They were suspended in 2.5 mL of water and stored at 5°.

Example 3

This example demonstrates that the compositions produced by the methods of the inventions, particularly those methods in which nucleotides are linked to a phosphor, that the nucleotide attached to the composition can be detected directly by techniques such as PCR. The phosphor compound utilized in this example was Yttrium oxysulfide as well as an amine linked DNA oligomer.

Detection of Bound DNA to Phosphor Particles by Real-Time-PCR.

The equipment and supplies utilized for RT-PCR were the following. PCR capillary system (20 ul capillary) by Roche Diagnostics, LightCycler 2 by Roche Diagnostics, SYBR Green ReadyMix RT-PCR kit by Sigma-Aldrich and SYBR Green JumpStart Tag mix by Sigma.

The following primers were specifically designed for amplification of the DNA oligomer attached to the phosphor particles produced by the methods of the invention. Primer 1-(5'-CGCCAGGGT TTTCCCAGTCACGAC-3') and Primer 2 (5'-CAGGAAACAGCTATGAC-3'). The final concentration of the primers for RT-PCR amplification was 0.05 uM in the RT-PCR rxn sample. The size of the amplicon generated during RT-PCR with this primer pair was approximately 150 bp in length.

The RT-PCR run conditions were as follows. One preheating cycle of 95° C. for 5 minutes, followed by 40 cycles of 20 seconds at 95° C., 40 seconds at the annealing temperature of 50° C., with polymerase extension at 72° C. for 20 seconds.

The isolated phosphor particles containing DNA molecules were resuspended in and diluted 1/10, 1/100, and 1/1000, respectively for RT-PCR analysis. Each RT-PCR sample contained 15 ul of RT-PCR master mix 0.5 ul of each Primer stock solution, 1 ul of a specified diluted phosphor containing DNA sample, and 13 ul water were mixed and put into 20 ul capillary tubes. Positive and Negative controls were also prepared. Duplicates of all RT-PCR samples were prepared and analyzed.

Figure 2:
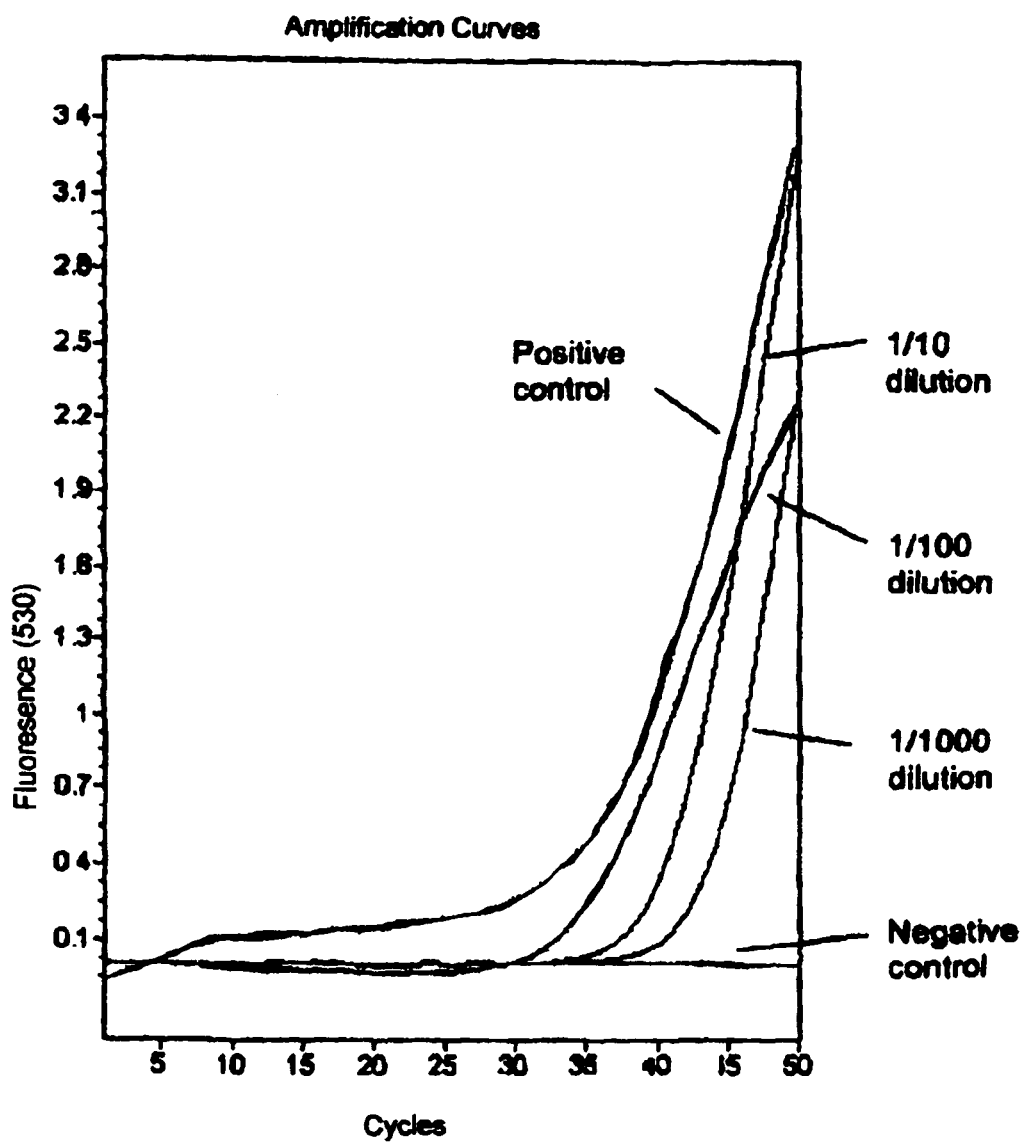
FIG. 2 is a plot of a real-time PCR results for a composition of the invention, comprising an optical reporter linked to a sequenceable DNA molecule.

The results from the RT-PCR experiment are shown in FIG. 2. The results in FIG. 2 show that the 1/100 dilution sample had a Ct of 30, while the 1/10 and 1/1000 dilution had a Ct of 33 and Ct of 36, respectively. At the 1/10 dilution the concentration of the UCP particles is high enough to quench the PCR signal, thus delaying the cycle in which amplification of the target DNA is present.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A composition of the formula I:

$$(cOpR)\text{-}[L\text{-}(NA)]_m \qquad I$$

wherein:
  m is an integer greater than 1;
  (cOpR) is a coated optical reporter particle, wherein the cOpR comprises an upconverting phosphor (UCP) material of the formula $Na(Y_xYb_yEr_z)F_4$, and wherein:
    x is from about 0.6 to about 0.95;
    y is from about 0.05 to about 0.35; and
    z is from about 0.1 to about 0.001;
  (NA) is a nucleic acid oligomer of detectable sequence; and
  L is a linking group covalently bound to the coated optical reporter particle and to the nucleic acid oligomer;
  provided that at least one of the following applies:
    x is not from 0.7 to 0.9; and/or
    y is not from 0.08 to 0.29; and/or
    z is not from 0.01 to 0.06.

2. The composition of claim 1, wherein (NA) is a single stranded DNA molecule having a length of between about 40 nucleotides and about 1000 nucleotides or a double stranded DNA molecule having a length of between about 40 base pairs and about 1000 base pairs.

3. The composition of claim 1, wherein L comprises an alkylene moiety having a first end covalently bound to the coated optical reporter particle and a second end covalently bound to the nucleic acid oligomer.

4. The composition of claim 1, wherein L is of the formula:

$$\text{—A-R}^1\text{—B—}$$

wherein:
  $R^1$ is $C_{2-8}$alkylene;
  -A- is a group covalently bonded to the surface of the coated optical reporter; and
  —B— is a group covalently bonded to the 3' or 5' end of the nucleic acid oligomer.

5. The composition of claim 4, wherein -A- is —O—.

6. The composition of claim 4, wherein —$R^1$— is —$(CH_2)_n$— and wherein n is from 2 to 8.

7. The composition of claim 4, wherein —B— is:

—S—;

—O—;

—$NR^a$—;

—S—$(CH_2)_p$—;

—O—$(CH_2)_p$—;

—$NR^a$—$(CH_2)_p$—;

—S—$(CH_2)_q$—C(O)—$NR^a$—$(CH_2)_p$—;

—O—$(CH_2)_q$—C(O)—$NR^a$—$(CH_2)_p$—;

—$NR^a$—$(CH_2)_q$—C(O)—$NR^a$—$(CH_2)_p$—;

—S—C(O)—$(CH_2)_r$—C(O)—$NR^a$—$(CH_2)_p$—;

—O—C(O)—$(CH_2)_r$—C(O)—$NR^a$—$(CH_2)_p$—; or

—$NR^a$—C(O)—$(CH_2)_r$—C(O)—$NR^a$—$(CH_2)_p$—;

wherein:
  p is from 2 to 8;
  q is from 1 to 8;
  r is from 2 to 8; and
  each $R^a$ is independently hydrogen or $C_{1-6}$alkyl.

8. The composition of claim 4, wherein —B— is:

—S—$(CH_2)_q$—C(O)—$NR^a$—$(CH_2)_p$ or

—$NR^a$—C(O)—$(CH_2)_r$—C(O)—$NR^a$—$(CH_2)_p$;

wherein:
  p is from 2 to 8;
  q is from 1 to 8;
  r is from 2 to 8; and
  each $R^a$ is independently hydrogen or $C_{1-6}$alkyl.

9. The composition of claim 8, wherein:
  p is from 2 to 6;
  q is from 1 to 3; and
  r is 2 or 3.

10. The composition of claim 4, wherein —B— is:

—S—$CH_2$—C(O)—NH—$(CH_2)_6$—; or

—NH—C(O)—$(CH_2)_3$—C(O)—NH—$(CH_2)_6$—.

11. The composition of claim 1, wherein the cOpR is coated with silica.

12. A composition of the formula II:

(UCP)-[A-$R^1$—X—$R^2$—C(O)—$NR^a$—$R^3$-(DNA)]$_m$    II wherein:
  m is an integer greater than 1;
  UCP is an upconverting phosphor particle of the formula $Na(Y_xYb_yEr_z)F_4$, wherein:
    x is from about 0.6 to about 0.95;
    y is from about 0.05 to about 0.35; and
    z is from about 0.1 to about 0.001;
  DNA is a single or double stranded deoxyribonucleic acid oligomer;
  -A- is a group covalently bound to a surface of the UCP;
  $R^1$ is $C_{2-8}$alkylene,
  $R^2$ is $C_{1-8}$alkylene or —C(O)—$C_{1-8}$alkylene-;
  —X— is —O—, —S— or —$NR^a$—;
  $R^3$ is $C_{2-8}$alkylene; and
  $R^a$ is hydrogen or $C_{1-6}$alkyl;
  provided that at least one of the following applies:
    x is not from 0.7 to 0.9; and/or
    y is not from 0.08 to 0.29; and/or
    z is not from 0.01 to 0.06.

13. The composition of claim 12, wherein the composition is of the formula IV:

(UCP)—[O—$(CH_2)_s$—S—$(CH_2)_t$—C(O)—NH—$(CH_2)_v$-(DNA)]$_m$    IV wherein:
  s is from 2 to 6;
  v is from 2 to 6; and
  t is from 1 to 3.

14. The composition of claim 12, wherein the composition is of the formula V:

(UCP)—[O—$(CH_2)_s$—NH—C(O)—$(CH_2)_u$—C(O)—NH—$(CH_2)_v$-(DNA)]$_m$    V wherein:
  s is from 2 to 6;
  v is from 2 to 6; and
  u is 2 or 3.

15. The composition of claim 12, wherein the composition is of the formula VI:

(UCP)—[O—$(CH_2)_3$—S—$CH_2$—C(O)—NH—$(CH_2)_6$-(DNA)]$_m$    VI.

16. The composition of claim 12, wherein the composition is of the formula VII:

(UCP)—[O—$(CH_2)_3$—NH—C(O)—$(CH_2)_3$—C(O)—NH—$(CH_2)_6$-(DNA)]$_m$    VII.

17. The composition of claim 1, wherein the cOpR comprises a visually detectable light emitting material selected from the group consisting of a fluorescent dye, a ceramic powder, or a quantum dot.

18. The composition of claim 17, where said light emitting materials are excitable by a UV light source or an infrared light source.

19. The composition of claim 1, wherein the cOpR comprises at least one electromagnetic radiation-emitting material.

20. The composition of claim 19, where the electromagnetic radiation-emitting material is detectable by devices which provide sources selected from the group consisting of an infrared radiation source, magnetic field source, a quantum dot or electromagnetic pulse.

21. A composition of the formula I:

(cOpR)-[L-(NA)]$_m$    I wherein:
  m is an integer greater than 1;
  (cOpR) is a coated optical reporter particle, wherein the cOpR comprises an upconverting phosphor (UCP) material of the formula $Na(Y_xYb_yEr_z)F_4$, and wherein:
    x is from about 0.6 to about 0.95;
    y is from about 0.05 to about 0.35; and
    z is from about 0.1 to about 0.001;

(NA) is a nucleic acid oligomer; and
L is a linking group covalently bound to the coated optical reporter particle and to the nucleic acid oligomer, wherein the linking group L comprises an alkylene moiety having a first end covalently bound to the coated optical reporter particle and a second end covalently bound to the nucleic acid oligomer.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Unknown
<220> FEATURE:
<223> OTHER INFORMATION: primer artificial sequence

<400> SEQUENCE: 1
cgccagggtt ttcccagtca cgac                                          24

<210> SEQ ID NO 2
<211> LENGTH: 17
<212> TYPE: DNA
<213> ORGANISM: Unknown
<220> FEATURE:
<223> OTHER INFORMATION: primer artificial sequence

<400> SEQUENCE: 2
caggaaacag ctatgac                                                  17